US006218169B1

(12) United States Patent
Cahoon et al.

(10) Patent No.: US 6,218,169 B1
(45) Date of Patent: Apr. 17, 2001

(54) AROMATIC AMINO ACID CATABOLISM ENZYMES

(75) Inventors: Rebecca E. Cahoon, Wilmington; Saverio Carl Falco, Arden, both of DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/362,473

(22) Filed: Jul. 28, 1999

Related U.S. Application Data

(60) Provisional application No. 60/094,783, filed on Jul. 31, 1998.

(51) Int. Cl.[7] .............................. C12N 1/20; C12N 9/00; C12N 9/02; C12N 9/04; C07H 21/04
(52) U.S. Cl. ...................... 435/252.3; 435/183; 435/189; 435/190; 536/23.2
(58) Field of Search ................................. 435/183, 252.3, 435/189, 190; 536/23.2

(56) References Cited

PUBLICATIONS

Newman T. et al. Plant Physiology vol. 106(4):1241–1255, 1994.*
Fernandez CJM. et al. Molecular characterization of a gene encoding a homogentisate dioxygenase from *Aspergillus nidulans* and identification of it human and plant homologues. J. Biol. Chem. vol. 270(36):21190–21205, 1995.*
Schmidt SR. et al. Cloning of the homogentisate 1,2–dioxygenase gene, the key enzyme of alkaptonuria in mouse. Mammalian Genome. vol. 8:168–171, 1997.*
Fernandez–Canon, J. M. et al., "The Molecular Basis of Alkaptonuria ", (Sep. 1996), Nat. Genet 14: 19–24.

Jose M. Fernandez–Canon et al., "Molecular Characterization of a Gene Encoding a Homogentisate Dixoygenase from *Aspergillus nidulans* and Identification of Its Human and Plant Homologues", (1995) J. Biol. Chem. 270(36):21199–21205.
St–Louis, M. and Tanguay, R. M., "Mutations in the Fumarylacetoacetate Hydrolase Gene Causing Hereditary Tyrosinemia Type I: Overview", (1997) Hum. Mut. 9:291–299.
Labelle, Y. et al. "Characterization of the Human Fumarylacetoacetate Hydrolase Gene Identification of a Missense Mutation Abolishing Enzymatic Activity", (1993) Hum. Mol. Genet. 2(7):941–946.
NCBI General Identifier No. 4098647, May 1, 1999.
NCBI General Identifier No. 4714775, Apr. 29,1999.
NCBI General Identifier No. 3157928, May 28, 1998.
NCBI General Identifier No. 4730752, Apr. 30, 1999.
NCBI General Identifier No. 4969133, Jun. 2, 1999.
NCBI General Identifier No. 2312281, Aug. 6, 1997.
NCBI General Identifier No. 4292828, Mar. 9, 1999.
NCBI General Identifier No. 4397647, Mar. 11, 1999.
Schmidt S. R., "Murine Liver Homogentisate 1,2–dioxygenase ", (1995) Eur. J. Biochem. 228:425–430.
Nagainis, M. P. et al., "Effects of pH and Sulfhydryl Specific Reagents on 4–Fumarylacetoacetate Fumarylhydrolase", (1981) Biochem. Biophys. Acta 657:203–211.

* cited by examiner

Primary Examiner—Ponnathapu Achutamurthy
Assistant Examiner—Manjunath Rao

(57) ABSTRACT

This invention relates to an isolated nucleic acid fragment encoding an aromatic amino acid catabolic enzyme. The invention also relates to the construction of a chimeric gene encoding all or a portion of the aromatic amino acid catabolic enzyme, in sense or antisense orientation, wherein expression of the chimeric gene results in production of altered levels of the aromatic amino acid catabolic enzyme in a transformed host cell.

5 Claims, No Drawings

AROMATIC AMINO ACID CATABOLISM ENZYMES

This application claims the benefit of U.S. Provisional Application Ser. No. 60/094,783, filed Jul. 31, 1998.

FIELD OF THE INVENTION

This invention is in the field of plant molecular biology. More specifically, this invention pertains to nucleic acid fragments encoding enzymes involved in aromatic amino acid catabolism in plants and seeds.

BACKGROUND OF THE INVENTION

In addition to their role as protein monomeric units, amino acids are energy metabolites and precursors of many biologically important nitrogen-containing compounds, such as heme, physiologically active amines, glutathione, other amino acids, nucleotides, and nucleotide coenzymes. Excess dietary amino acids are neither stored for future use nor excreted. Rather they are converted to common metabolic intermediates such as pyruvate, oxaloacetate, and alpha-ketoglutarate. Consequently, amino acids are also precursors of glucose, fatty acids, and ketone bodies and are therefore metabolic fuels. The degradation of amino acids converts them to citric acid cycle intermediates or their precursors so that they can be metabolized to $CO_2$ and water or used in gluconeogenesis. Oxidative breakdown of amino acids typically accounts for 10 to 15% of the metabolic energy generated by animals.

The enzymes included in this application are involved in catabolism of the aromatic amino acids. The first reaction in phenylalanine degradation is its hydroxylation to tyrosine; thus a single pathway is responsible for the breakdown of both of these amino acids. 3,4-Dehydroxyphenyl acetate 2,3-dioxygenase is also called homogentisate 1,2-dioxygenase (EC 1.13.11.15) and, in the presence of oxygen, catalyzes the decyclization of homogentisic acid (3,4-dihydroxyphenylacetate) into 2-Hydroxy-5-carboxymethylmuconate semialdehyde. Loss of homogentisate 1,2 dioxygenase (HGO) activity is responsible for the human metabolic disorder alkaptonuria. A large number of variant forms of the human enzyme have been described which show the clinical effect of single nucleotide changes on the activity of the enzyme (Fernandez-Canon, J. M. et al. (1996). *Nat Genet* 14:19–24). The gene *Aspergillus nidulans* homogentisate 1,2 dioxygenase has been characterized and its disruption shown to induce secretion of homogenistate ((1995) *J. Biol Chem* 270:21199–21205). In the same article, the authors searched the GenBank database with the homogentisate 1,2 dioxygenase sequence and identified ESTs with significant similarity to homogentisate 1,2 dioxygenase. These ESTs were from tissues obtained from human, *Arabidopsis thaliana,* and *Ricinus communis.*

Fumarylacetoacetase, also named fumarylacetoacetate hydrolase (EC 3.7.1.2) catalyzes the last step in the phenylalanine/tyrosine degradation catalyzing the conversion of 4-fumarylacetoacetate and water to acetoacetate and fumarate. Debilitating mutations in this enzyme have been shown to be the cause of hereditary tyrosinemia type I in humans (St-Louis, M. and Tanguay, R. M. (1997) *Hum. Mut.* 9:291–299; Labelle, Y. et al. (1993) *Hum. Mol. Genet.* 2:941–946).

SUMMARY OF THE INVENTION

The instant invention relates to isolated nucleic acid fragments encoding enzymes involved in aromatic amino acid catabolism. Specifically, this invention concerns an isolated nucleic acid fragment encoding a homogentisate 1,2-dioxygenase or a fumarylacetoacetase and an isolated nucleic acid fragment that is substantially similar to an isolated nucleic acid fragment encoding a homogentisate 1,2-dioxygenase or a fumarylacetoacetase. In addition, this invention relates to a nucleic acid fragment that is complementary to the nucleic acid fragment encoding homogentisate 1,2-dioxygenase or fumarylacetoacetase.

An additional embodiment of the instant invention pertains to a polypeptide encoding all or a substantial portion of an enzyme involved in aromatic amino acid catabolism selected from the group consisting of homogentisate 1,2-dioxygenase and fumarylacetoacetase.

In another embodiment, the instant invention relates to a chimeric gene encoding a homogentisate 1,2-dioxygenase or a fumarylacetoacetase, or to a chimeric gene that comprises a nucleic acid fragment that is complementary to a nucleic acid fragment encoding a homogentisate 1,2-dioxygenase or a fumarylacetoacetase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a homogentisate 1,2-dioxygenase or a fumarylacetoacetase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a homogentisate 1,2-dioxygenase or a fumarylacetoacetase in a transformed host cell comprising: a) transforming a host cell with a chimeric gene comprising a nucleic acid fragment encoding a homogentisate 1,2-dioxygenase or a fumarylacetoacetase; and b) growing the transformed host cell under conditions that are suitable for expression of the chimeric gene wherein expression of the chimeric gene results in production of altered levels of homogentisate 1,2-dioxygenase or fumarylacetoacetase in the transformed host cell.

An addition embodiment of the instant invention concerns a method for obtaining a nucleic acid fragment encoding all or a substantial portion of an amino acid sequence encoding a homogentisate 1,2-dioxygenase or a fumarylacetoacetase.

A further embodiment of the instant invention is a method for evaluating at least one compound for its ability to inhibit the activity of a homogentisate 1,2-dioxygenase or a fumarylacetoacetase, the method comprising the steps of: (a) transforming a host cell with a chimeric gene comprising a nucleic acid fragment encoding a homogentisate 1,2-dioxygenase or a fumarylacetoacetase, operably linked to suitable regulatory sequences; (b) growing the transformed host cell under conditions that are suitable for expression of the chimeric gene wherein expression of the chimeric gene results in production of homogentisate 1,2-dioxygenase or fumarylacetoacetase in the transformed host cell; (c) optionally purifying the homogentisate 1,2-dioxygenase or the fumarylacetoacetase expressed by the transformed host cell; (d) treating the homogentisate 1,2-dioxygenase or the fumarylacetoacetase with a compound to be tested; and (e) comparing the activity of the homogentisate 1,2-dioxygenase or the fumarylacetoacetase that has been treated with a test compound to the activity of an untreated homogentisate 1,2-dioxygenase or fumarylacetoacetase, thereby selecting compounds with potential for inhibitory activity.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Enzymes Involved in Aromatic Amino Acid Catabolism

| Protein | Clone Designation | SEQ ID NO: | |
|---|---|---|---|
| | | (Nucleotide) | (Amino Acid) |
| Homogentisate 1,2-Dioxygenase | cbn2.pk0052.e6 | 1 | 2 |
| | rls6.pk0027.h11 | 3 | 4 |
| | sfl1.pk0008.h2 | 5 | 6 |
| | wlk8.pk0020.a11 | 7 | 8 |
| Fumarylacetoacetase | Contig of: cc71se-b.pk0004.b5 cr1n.pk0107.d3 cr1n.pk0151.e7 | 9 | 10 |
| | rl0n.pk082.n4 | 11 | 12 |
| | sgs6c.pk001.h5 | 13 | 14 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) *Nucleic Acid Hybridisation*, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. A set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 60° C. for 30 min. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several enzymes involved in aromatic amino acid catabolism have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other homogentisate 1,2-dioxygenases, fumaryl-acetoacetases or nitrile hydratases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36: 1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of aromatic amino acids or their intermediates in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded aromatic amino acid catabolic enzymes. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in aromatic amino acid catabolism. Accordingly, inhibition of the activity of one or more of the enzymes described herein could lead to inhibition plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries, Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cbn2 | Corn Developing Kernel Two Days After Pollination | cbn2.pk0052.e6 |
| cc71se-b | Corn Callus Type II Tissue, Somatic Embryo Formed | cc71se-b.pk0004.b5 |
| cr1n | Corn Root From 7 Day Old Seedlings* | cr1n.pk0107.d3 cr1n.pk0151.e7 |
| rl0n | Rice 15 Day Old Leaf* | rl0n.pk082.n4 |
| rls6 | Rice Leaf 15 Days After Germination, 6 Hours After Infection of Strain *Magaporthe grisea* 4360-R-67 (AVR2-YAMO); Susceptible | rls6.pk0027.h11 |
| sfl1 | Soybean Immature Flower | sfl1.pk0008.h2 |
| sgs6c | Soybean Seeds 8 Days After Germination | sgs6c.pk001.h5 |
| wlk8 | Wheat Seedlings 8 Hours After Treatment With Herbicide** | wlk8.pk0020.a11 |

*These libraries were normalized essentially as described in U.S. Pat. No. 5,482,845, incorporated herein by reference.
**Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding enzymes involved in aromatic amino acid catabolism were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Homogentisate 1,2-Dioxygenase

The BLASTX search using the EST sequences from clones listed in Table 3 revealed similarity of the polypeptides encoded by the cDNAs to homogentisate 1,2-dioxygenase from *Arabidopsis thaliana* (NCBI General Identifier No. 4098647). Shown in Table 3 are the BLAST results for the sequences of the entire cDNA inserts comprising the indicated cDNA clones ("FIS"):

TABLE 3

BLAST Results for Sequences Encoding Polypeptides Homologous to Homogentisate 1,2-Dioxygenase

| Clone | Status | BLAST pLog Score 4098647 |
|---|---|---|
| cbn2.pk0052.e6 | FIS | 254.00 |
| rls6.pk0027.h11 | FIS | 254.00 |

TABLE 3-continued

BLAST Results for Sequences Encoding Polypeptides Homologous to Homogentisate 1,2-Dioxygenase

| Clone | Status | BLAST pLog Score 4098647 |
|---|---|---|
| sfl1.pk0008.h2 | FIS | 254.00 |
| wlk8.pk0020.a11 | FIS | 133.00 |

Nucleotides 952 through 1656 from clone cbn2.pk0052.e6 are 99% identical to nucleotides 1 through 705 of a 719 nt rice EST having NCBI General Identifier No. 4714775. Nucleotides 255 through 613 are 85% identical to nucleotides 1 through 359 of a 719 nt rice EST having NCBI General Identifier No. 4714775. The data in Table 4 represents a calculation of the percent identity of the amino acid sequences set forth in SEQ ID NOs:2, 4, 6 and 8 and the Arabidopsis thaliana sequence (SEQ ID NO:9).

TABLE 4

Percent Identity of Amino Acid Sequences Deduced From the Nucleotide Sequences of cDNA Clones Encoding Polypeptides Homologous to Homogentisate 1,2-Dioxygenase

| SEQ ID NO. | Percent Identity to 4098647 |
|---|---|
| 2 | 73.2 |
| 4 | 72.7 |
| 6 | 76.3 |
| 8 | 76.2 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode entire corn, rice and soybean homogentisate 1,2-dioxygenase and a substantial portion of a wheat homogentisate 1,2-dioxygenase. These sequences represent the first corn, rice, soybean and wheat sequences encoding homogentisate 1,2-dioxygenase.

Example 4

Characterization of cDNA Clones Encoding Fumarylacetoacetase

The BLASTX search using the EST sequences from clones listed in Table 5 revealed similarity of the polypeptides encoded by the cDNAs to fumarylacetoacetase from Arabidopsis thaliana (NCBI General Identifier No. 3157928). Shown in Table 5 are the BLAST results for the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to Fumarylacetoacetase

| Clone | Status | BLAST pLog Score 3157928 |
|---|---|---|
| Contig of:<br>cc71se-b.pk0004.b5<br>cr1n.pk0107.d3<br>cr1n.pk0151.e7 | Contig | 107.00 |
| r10n.pk082.n4 | FIS | 169.00 |
| sgs6c.pk001.h5 | FIS | 180.00 |

Nucleotides 457 through 842 from the corn contig (SEQ ID NO:9) are 92% identical to nucleotides 599 through 212 of a corn EST having NCBI General Identifier No. 4730752. Nucleotides 414 through 782 from rice clone r10n.pk082.n4 are 99% identical to nucleotides 1 through 369 of a 382 nt rice EST having NCBI General Identifier No. 4969133. Nucleotides 53 to 329 from the same clone are 97% identical to nucleotides 1 through 277 of a 277 nt rice EST having NCBI General Identifier No. 2312281. Nucleotides 993 through 1310 from clone sgs6c.pk001.h5 are 94% identical to nucleotides 156 through 473 of a 474 nt soybean EST having NCBI General Identifier No.4292828. Nucleotides 1117 through 1304 from the same clone are 92% identical to nucleotides 1 through 189 or a 393 soybean EST having NCBI General Identifier No. 9397647. The data in Table 6 represents a calculation of the percent identity of the amino acid sequences set forth in SEQ ID NOs: 11, 13 and 15 and the *Arabidopsis thaliana* sequence (SEQ ID NO: 16).

TABLE 6

Percent Identity of Amino Acid Sequences Deduced From the Nucleotide Sequences of cDNA Clones Encoding Polypeptides Homologous to Fumarylacetoacetase

| SEQ ID NO. | Percent Identity to 3157928 |
|---|---|
| 10 | 63.0 |
| 12 | 65.0 |
| 14 | 71.1 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn fumarylacetoacetase and entire rice and soybean fumarylacetoacetase. These sequences represent the first corn, rice and soybean sequences encoding fumarylacetoacetase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Aromatic Amino Acid Catabolism Enzymes The polypeptides described herein may be produced using any number of methods known to those skilled in the art.

Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for homogentisate 1,2-dioxygenase are presented by Schmidt S. R. (1995) *Eur. J. Biochem.* 1995 228:425–430. Assays for fumarylacetoacetase are presented by Nagainis M. P. et al. (1981) *Biochim. Biophys. Acta* 657:203–211.

What is claimed is:

1. An isolated nucleic acid fragment comprising a member selected from the group consisting of:
   (a) an isolated nucleic acid fragment encoding the amino acid sequence set forth in a member selected from the group consisting of SEQ ID NO:2, SEQ ID NO:4, SEQ ID NO:6, SEQ ID NO:8; and
   (b) an isolated nucleic acid fragment that is complementary to (a).

2. The isolated nucleic acid fragment of claim 1 wherein nucleic acid fragment is a RNA.

3. The isolated nucleic acid fragment of claim 1 wherein the nucleotide sequence of the fragment comprises the sequence set forth in a member selected from the group consisting of SEQ ID NO:1, SEQ ID NO:3, SEQ ID NO:5 and SEQ ID NO:7.

4. A chimeric gene comprising the nucleic acid fragment of claim 1 operably linked to suitable regulatory sequences.

5. A transformed host cell comprising the chimeric gene of claim 4.

* * * * *

SEQUENCE LISTING

<160> NUMBER OF SEQ ID NOS: 14

<210> SEQ ID NO 1
<211> LENGTH: 1651
<212> TYPE: DNA
<213> ORGANISM: Zea mays

<400> SEQUENCE: 1

```
gcacgagctt ggatcctcga caagcaatgg ccatggagga ggagcagaca ccacccgagc      60
tgcgctacct ctcgggcctg ggcaacacct tcacgtcgga ggcggtgccg gggtcgctcc     120
ccgtggggca gaacaacccg ctagtgtgcc cgctgggact ctacgccgag cagctctccg     180
gcacctcctt caccaccccg cgcgcccgga acctgcgcac gtggctgtac cggatcaagc     240
cgtcggtgac ccacgaaccc ttctatccgc ggaacccac caacgagcgc ctcgtcggcg      300
agttcgaccg caccaccacc gtcgccacgc ccacgcagct gcgctggagg cccgccgacg     360
tgcccctcca cccgggcctc gacttcatcg acggactcta caccgtctgc ggcgccggca     420
gctcatgcct ccgacacgga tacgccatcc acatgtatgc tgctaacacg cccatggatg     480
gatgctcctt gtgcaatgcg gacggtgact tcctcattgt tccccagcaa ggaaggttat     540
ttatcacaac cgagtgcgga aggctgctgg tttcaccgg cgagatcgtc gtgatccctc     600
aaggtctccg atttgctgtc gacttgccgg atggcccctc gcgtggctat gtctctgaga     660
tcttcggcgc ccattttcag ctccctgatc ttggcccaat tggtgccaat ggcttggctt     720
cgccgaggga tttcctttcc ccgacagcat ggtttgagca ggagcaccac cctggataca     780
caatagtgca caagtatggt ggcgagctgt tcagcgccac gcaggatttc tctccattca     840
```

```
acgtggtcgc gtggcatggg aattatgtcc cttacaagta tgatctgagt aagttctgtc    900
cattcaacac cgtcctcttg gatcatggcg acccgtcagt gaacacagtt ctaactgcgc    960
caactgataa gcctggcgtc gcgttgcttg attttgtaat attcccaccc agatggctgg   1020
ttgctgagaa tacattccgc ccaccctact accaccgcaa ctgcatgagc gaattcatgg   1080
gcctcatcta tgggatgtac gaggctaagg ccgatggttt tcttcctggt ggcgccagcc   1140
ttcacagctg catgacaccg catgggccag acaccaagac gtacgaggca cgatcagcc   1200
gtgctgctgc caacgagcca tccaggctca gtggtacgtt ggcgttcatg tttgagtctt   1260
ggcttatccc tcgcgtgtgc ccatgggctc tggattcccc gtgtcgggac ctcgactact   1320
accagtgctg gatcggattg aagtcacact tttcacctcc tgctgctgct gttgatgatg   1380
agaacgagta gctgcttaca gcagcagtct tggaacggac aggcagcgaa ctgaaactgg   1440
ggtggatatg ctgtacgtcg tgtcctgctt gctgtcggtt tctgaagctt ttagctggca   1500
gggacaggcg gctgttggct ttgctgattg cccaacccct cctgtaata ttaatcctac   1560
cagagaaact taaacttgac tcaaccgata tgctattaaa taaataaagc aagcaagtta   1620
ggatacgagt taaaaaaaaa aaaaaaaaaa a                                   1651
```

<210> SEQ ID NO 2
<211> LENGTH: 454
<212> TYPE: PRT
<213> ORGANISM: Zea mays

<400> SEQUENCE: 2

```
Met Ala Met Glu Glu Glu Gln Thr Pro Pro Glu Leu Arg Tyr Leu Ser
  1               5                  10                  15

Gly Leu Gly Asn Thr Phe Thr Ser Glu Ala Val Pro Gly Ser Leu Pro
                 20                  25                  30

Val Gly Gln Asn Asn Pro Leu Val Cys Pro Leu Gly Leu Tyr Ala Glu
             35                  40                  45

Gln Leu Ser Gly Thr Ser Phe Thr Thr Pro Arg Ala Arg Asn Leu Arg
         50                  55                  60

Thr Trp Leu Tyr Arg Ile Lys Pro Ser Val Thr His Glu Pro Phe Tyr
 65                  70                  75                  80

Pro Arg Asn Pro Thr Asn Glu Arg Leu Val Gly Glu Phe Asp Arg Thr
                 85                  90                  95

Thr Thr Val Ala Thr Pro Thr Gln Leu Arg Trp Arg Pro Ala Asp Val
            100                 105                 110

Pro Leu His Pro Gly Leu Asp Phe Ile Asp Gly Leu Tyr Thr Val Cys
        115                 120                 125

Gly Ala Gly Ser Ser Cys Leu Arg His Gly Tyr Ala Ile His Met Tyr
    130                 135                 140

Ala Ala Asn Thr Pro Met Asp Gly Cys Ser Leu Cys Asn Ala Asp Gly
145                 150                 155                 160

Asp Phe Leu Ile Val Pro Gln Gln Gly Arg Leu Phe Ile Thr Thr Glu
                165                 170                 175

Cys Gly Arg Leu Leu Val Ser Pro Gly Glu Ile Val Val Ile Pro Gln
            180                 185                 190

Gly Leu Arg Phe Ala Val Asp Leu Pro Asp Gly Pro Ser Arg Gly Tyr
        195                 200                 205

Val Ser Glu Ile Phe Gly Ala His Phe Gln Leu Pro Asp Leu Gly Pro
    210                 215                 220

Ile Gly Ala Asn Gly Leu Ala Ser Pro Arg Asp Phe Leu Ser Pro Thr
```

```
                225                 230                 235                 240
Ala Trp Phe Glu Gln Glu His His Pro Gly Tyr Thr Ile Val His Lys
                    245                 250                 255
Tyr Gly Gly Glu Leu Phe Ser Ala Thr Gln Asp Phe Ser Pro Phe Asn
                260                 265                 270
Val Val Ala Trp His Gly Asn Tyr Val Pro Tyr Lys Tyr Asp Leu Ser
            275                 280                 285
Lys Phe Cys Pro Phe Asn Thr Val Leu Leu Asp His Gly Asp Pro Ser
        290                 295                 300
Val Asn Thr Val Leu Thr Ala Pro Thr Asp Lys Pro Gly Val Ala Leu
305                 310                 315                 320
Leu Asp Phe Val Ile Phe Pro Pro Arg Trp Leu Val Ala Glu Asn Thr
                    325                 330                 335
Phe Arg Pro Pro Tyr Tyr His Arg Asn Cys Met Ser Glu Phe Met Gly
                340                 345                 350
Leu Ile Tyr Gly Met Tyr Glu Ala Lys Ala Asp Gly Phe Leu Pro Gly
            355                 360                 365
Gly Ala Ser Leu His Ser Cys Met Thr Pro His Gly Pro Asp Thr Lys
        370                 375                 380
Thr Tyr Glu Ala Thr Ile Ser Arg Ala Ala Asn Glu Pro Ser Arg
385                 390                 395                 400
Leu Ser Gly Thr Leu Ala Phe Met Phe Glu Ser Trp Leu Ile Pro Arg
                    405                 410                 415
Val Cys Pro Trp Ala Leu Asp Ser Pro Cys Arg Asp Leu Asp Tyr Tyr
                420                 425                 430
Gln Cys Trp Ile Gly Leu Lys Ser His Phe Ser Pro Pro Ala Ala Ala
            435                 440                 445
Val Asp Asp Glu Asn Glu
    450

<210> SEQ ID NO 3
<211> LENGTH: 1694
<212> TYPE: DNA
<213> ORGANISM: Oryza sativa

<400> SEQUENCE: 3
gcacgaggtt ctaacgagaa gcctcctgaa actgaaagga gacaagcagt tgtgttgtcc    60
ttctccctct cctccggcca gcggccatgg ccatggcaac ggcaaccccc gcggcgcaga   120
atgagcagca ggagaagggg gggttggagt acgtatatct gtcggggctg gcaacagct   180 tgtcgtcgga ggcggtggcg gggacgctcc cgcgcgggca gaacagcccg ctggtctgcc   240
cgctgggact ctacgccgag cagctctccg gcacgccctt caccgccccg cgcgcccgca   300
acctccgaac atggctgtac cggatcaagc cttcggtgac ccacgagccc ttccaccccc   360
gtcgccccgc ccaccccgc ctcattgggg atttcgaccg caccaccacc gacaccgtcg   420
ccacgcccac ccagctgcgc tggcgccccg ccgacgtgcc ccccaccat cctccctcg   480 atttcatcga tggcctctac accgtctgcg gcgctggcag ctccttcctg cgccacggat   540
acgccatcca catgtatgta tgtatgtacg ctgctaacaa gtccatggac ggatgcgcct   600
tttgcaacgc tgacggcgat ttcctcattg tcccccagca aggaaagctg ttgatcacaa   660
ctgaatgtgg gaagctgcta gtcccacctg gtgaaattgt tgtcattccc caggtttttc   720
gctttgctgt tgatttgccc gatggtcctt cacgtggcta tgtttctgag attttcggta   780
cccactttca gctccctgat cttggcccga ttggtgcaaa tggcttggct tcggcaaggg   840
```

-continued

```
atttcctttc cccaacagca tggtttgagc aagtccaccg cccaggatac acaattgtgc    900
agaaatatgg tggtgagcta ttcactgcca ctcaggactt ttctccattt aatgtggtag    960
cgtggcatgg aaattatgtc ccttacaagt acgacctgag taaattctgt ccatttaaca   1020
ctgttctatt cgatcatgct gatccatcag taaatacagt gctgactgca ccaactgata   1080
agcctggtgt cgcattgctt gattttgtga tattcccgcc tagatggttg gtcgctgaga   1140
acacatttcg ccctccatac tatcatcgca attgcatgag tgaatttatg ggattgatct   1200
atggaatata cgaggccaaa gctgatggtt ttcttcctgg aggtgctagc cttcacagtt   1260
gcatgacacc tcatggccca gacaccaaga catacgaggc aacaatcagc cgtcctgatg   1320
ccaatgagcc atcaaggcta agcggcacgc ttgcattcat gttcgagtct gcactcatcc   1380
ccagggtttg ccaatgggcc ctcgattccc catcccggga tctcgattac taccagtgct   1440
ggattggatt gaaatcccac ttctcacatg acaatggagg ggcaaccagc gaagaaccat   1500
gcagaaagta gctttgatca gttttagtag cttatgatgc tgtgcttgtg tatattttgt   1560
gaggctgtaa ctgaaccatt caccagatcc gtgtaagtaa agacaataat gctcagcagc   1620
ctgtactgta caatcgtggg tatagcatta tcagaagcaa gaatgtcaat ttcaataaaa   1680
aaaaaaaaaa aaaa                                                     1694
```

<210> SEQ ID NO 4
<211> LENGTH: 474
<212> TYPE: PRT
<213> ORGANISM: Oryza sativa

<400> SEQUENCE: 4

```
Met Ala Met Ala Thr Ala Thr Pro Ala Ala Gln Asn Glu Gln Gln Glu
  1               5                  10                  15

Lys Gly Gly Leu Glu Tyr Val Tyr Leu Ser Gly Leu Gly Asn Ser Leu
             20                  25                  30

Ser Ser Glu Ala Val Ala Gly Thr Leu Pro Arg Gly Gln Asn Ser Pro
         35                  40                  45

Leu Val Cys Pro Leu Gly Leu Tyr Ala Glu Gln Leu Ser Gly Thr Pro
     50                  55                  60

Phe Thr Ala Pro Arg Ala Arg Asn Leu Arg Thr Trp Leu Tyr Arg Ile
 65                  70                  75                  80

Lys Pro Ser Val Thr His Glu Pro Phe His Pro Arg Arg Pro Ala His
                 85                  90                  95

Pro Arg Leu Ile Gly Asp Phe Asp Arg Thr Thr Thr Asp Thr Val Ala
            100                 105                 110

Thr Pro Thr Gln Leu Arg Trp Arg Pro Ala Asp Val Pro Pro His His
        115                 120                 125

Pro Pro Leu Asp Phe Ile Asp Gly Leu Tyr Thr Val Cys Gly Ala Gly
    130                 135                 140

Ser Ser Phe Leu Arg His Gly Tyr Ala Ile His Met Tyr Val Cys Met
145                 150                 155                 160

Tyr Ala Ala Asn Lys Ser Met Asp Gly Cys Ala Phe Cys Asn Ala Asp
                165                 170                 175

Gly Asp Phe Leu Ile Val Pro Gln Gln Gly Lys Leu Leu Ile Thr Thr
            180                 185                 190

Glu Cys Gly Lys Leu Leu Val Pro Pro Gly Glu Ile Val Val Ile Pro
        195                 200                 205

Gln Gly Phe Arg Phe Ala Val Asp Leu Pro Asp Gly Pro Ser Arg Gly
```

```
              210                 215                 220
Tyr Val Ser Glu Ile Phe Gly Thr His Phe Gln Leu Pro Asp Leu Gly
225                 230                 235                 240

Pro Ile Gly Ala Asn Gly Leu Ala Ser Ala Arg Asp Phe Leu Ser Pro
                245                 250                 255

Thr Ala Trp Phe Glu Gln Val His Arg Pro Gly Tyr Thr Ile Val Gln
                260                 265                 270

Lys Tyr Gly Gly Glu Leu Phe Thr Ala Thr Gln Asp Phe Ser Pro Phe
                275                 280                 285

Asn Val Val Ala Trp His Gly Asn Tyr Val Pro Tyr Lys Tyr Asp Leu
                290                 295                 300

Ser Lys Phe Cys Pro Phe Asn Thr Val Leu Phe Asp His Ala Asp Pro
305                 310                 315                 320

Ser Val Asn Thr Val Leu Thr Ala Pro Thr Asp Lys Pro Gly Val Ala
                325                 330                 335

Leu Leu Asp Phe Val Ile Phe Pro Pro Arg Trp Leu Val Ala Glu Asn
                340                 345                 350

Thr Phe Arg Pro Pro Tyr Tyr His Arg Asn Cys Met Ser Glu Phe Met
                355                 360                 365

Gly Leu Ile Tyr Gly Ile Tyr Glu Ala Lys Ala Asp Gly Phe Leu Pro
370                 375                 380

Gly Gly Ala Ser Leu His Ser Cys Met Thr Pro His Gly Pro Asp Thr
385                 390                 395                 400

Lys Thr Tyr Glu Ala Thr Ile Ser Arg Pro Asp Ala Asn Glu Pro Ser
                405                 410                 415

Arg Leu Ser Gly Thr Leu Ala Phe Met Phe Glu Ser Ala Leu Ile Pro
                420                 425                 430

Arg Val Cys Gln Trp Ala Leu Asp Ser Pro Ser Arg Asp Leu Asp Tyr
                435                 440                 445

Tyr Gln Cys Trp Ile Gly Leu Lys Ser His Phe Ser His Asp Asn Gly
                450                 455                 460

Gly Ala Thr Ser Glu Glu Pro Cys Arg Lys
465                 470

<210> SEQ ID NO 5
<211> LENGTH: 1639
<212> TYPE: DNA
<213> ORGANISM: Glycine max

<400> SEQUENCE: 5
gcacgaggtt caattcttta ctcaaacttt gtgttcactc tttctctttt ttggtgttag      60
ttcggtgaat catggagaac ccaatcgacg gtggcgagtt cgtgtacctt ccgggttcg     120
gcaaccactt ctcctccgag gccctcgccg gagctctgcc ggtggcgcag aacagccccc     180
tcgtctgccc gtacggcctc tacgccgagc aaatctctgg cacctccttc acctcccctc     240
gcaaccgcaa cctcttcagt tggttttatc ggatcaagcc atcggtgact cacgaaccgt     300
tcaagcctag ggtacctggt aatggcagaa ttttgagtga gtttaacaac tccaacagtt     360
ctgctaaccc aactcagctt agatggaagc cttggatgc gcccgattcg ccaacagatt      420
tcattgatgg gttgtccact gtgtgtggtt ctggcagctc cttcatgcgc acggatatg      480
ctattcacat gtacactgcc aacaaatcaa tggacaattg tgccttttgc aatgctgatg     540
gtgacttctt gatagttccc caacaaggaa gactccttgt cactactgaa gtggaaggt      600
tgaaagtttc tccaggtgaa attgctatat acctcaaggg ctttcgtttt tctgtgaatc     660
```

```
ttcctgatgg tccatcccgt ggttatgttg ctgaaatttt tggtactcat tttcaacttc    720
ctgatctggg accaataggt gctaatggcc ttgcttcccc tagggatttc cttgttccca    780
ctgcttggtt tgaagataaa tcttatcctg gtacaccat agtgcagaaa tttggtggtg     840
agctctttga tgcagtacaa gatttctctc ctttcaatgt tgttgcttgg catggtaatt   900
atgttccata tatgtatgat ttaaacaaat tctgccctta taatacagtt ctgtttgatc   960
atagtgatcc atcaatcaat actgtgttga cagcaccaac tgataaacct ggagtggcat  1020
tgcttgattt tgtcattttc ccacccagat ggctggttgc tgagcatact ttccggcctc  1080
catattatca tcgcaattgc atgagtgaat ttatgggcct cattcatggt ggttatgagg  1140
ccaaggctga tggatttctt cccggtggtg caagtctcca tagttgtatg actccccatg  1200
gtcctgatac caagtcatat gaggctacca ttgcacgagg aaatgatgta ggaccttgca  1260
agatcactga cacaatggct tttatgtttg aatcgagttt gatacccgt atcagtcaat   1320 gggcctcaga atcaccgttc ttggaccaag attattacca gtgttggatt ggcctgaaat  1380
ctcattttgc agttactaag acgtctcctg aaaacccaag cttgggaaat ggagattgag  1440
gagtgaaatg ggtgttgcga cacaggcagt tagaccacca aaagattggg tttctttgta  1500
cataaaaata aatgtaatta caaaatata atttaggtgt gtcaaaagtg aactcaaccc    1560
aattggtggg aatcaaatgg tttcaggcaa gttttttaaa aaaaaaaaa aaaaaaaaa    1620 aaaaaaaaaa aaaaaaaaa                                                1639

<210> SEQ ID NO 6
<211> LENGTH: 455
<212> TYPE: PRT
<213> ORGANISM: Glycine max

<400> SEQUENCE: 6

Met Glu Asn Pro Ile Asp Gly Gly Glu Phe Val Tyr Leu Ser Gly Phe
  1               5                  10                  15

Gly Asn His Phe Ser Ser Glu Ala Leu Ala Gly Ala Leu Pro Val Ala
             20                  25                  30

Gln Asn Ser Pro Leu Val Cys Pro Tyr Gly Leu Tyr Ala Glu Gln Ile
         35                  40                  45

Ser Gly Thr Ser Phe Thr Ser Pro Arg Asn Arg Asn Leu Phe Ser Trp
     50                  55                  60

Phe Tyr Arg Ile Lys Pro Ser Val Thr His Glu Pro Phe Lys Pro Arg
 65                  70                  75                  80

Val Pro Gly Asn Gly Arg Ile Leu Ser Glu Phe Asn Asn Ser Asn Ser
                 85                  90                  95

Ser Ala Asn Pro Thr Gln Leu Arg Trp Lys Pro Leu Asp Ala Pro Asp
            100                 105                 110

Ser Pro Thr Asp Phe Ile Asp Gly Leu Ser Thr Val Cys Gly Ser Gly
        115                 120                 125

Ser Ser Phe Met Arg His Gly Tyr Ala Ile His Met Tyr Thr Ala Asn
    130                 135                 140

Lys Ser Met Asp Asn Cys Ala Phe Cys Asn Ala Asp Gly Asp Phe Leu
145                 150                 155                 160

Ile Val Pro Gln Gln Gly Arg Leu Leu Val Thr Thr Glu Cys Gly Arg
                165                 170                 175

Leu Lys Val Ser Pro Gly Glu Ile Ala Ile Leu Pro Gln Gly Phe Arg
            180                 185                 190
```

```
Phe Ser Val Asn Leu Pro Asp Gly Pro Ser Arg Gly Tyr Val Ala Glu
        195                 200                 205
Ile Phe Gly Thr His Phe Gln Leu Pro Asp Leu Gly Pro Ile Gly Ala
    210                 215                 220
Asn Gly Leu Ala Ser Pro Arg Asp Phe Leu Val Pro Thr Ala Trp Phe
225                 230                 235                 240
Glu Asp Lys Ser Tyr Pro Gly Tyr Thr Ile Val Gln Lys Phe Gly Gly
                245                 250                 255
Glu Leu Phe Asp Ala Val Gln Asp Phe Ser Pro Phe Asn Val Val Ala
            260                 265                 270
Trp His Gly Asn Tyr Val Pro Tyr Met Tyr Asp Leu Asn Lys Phe Cys
        275                 280                 285
Pro Tyr Asn Thr Val Leu Phe Asp His Ser Asp Pro Ser Ile Asn Thr
    290                 295                 300
Val Leu Thr Ala Pro Thr Asp Lys Pro Gly Val Ala Leu Leu Asp Phe
305                 310                 315                 320
Val Ile Phe Pro Pro Arg Trp Leu Val Ala Glu His Thr Phe Arg Pro
                325                 330                 335
Pro Tyr Tyr His Arg Asn Cys Met Ser Glu Phe Met Gly Leu Ile His
            340                 345                 350
Gly Gly Tyr Glu Ala Lys Ala Asp Gly Phe Leu Pro Gly Gly Ala Ser
        355                 360                 365
Leu His Ser Cys Met Thr Pro His Gly Pro Asp Thr Lys Ser Tyr Glu
    370                 375                 380
Ala Thr Ile Ala Arg Gly Asn Asp Val Gly Pro Cys Lys Ile Thr Asp
385                 390                 395                 400
Thr Met Ala Phe Met Phe Glu Ser Ser Leu Ile Pro Arg Ile Ser Gln
                405                 410                 415
Trp Ala Ser Glu Ser Pro Phe Leu Asp Gln Asp Tyr Tyr Gln Cys Trp
            420                 425                 430
Ile Gly Leu Lys Ser His Phe Ala Val Thr Lys Thr Ser Pro Glu Asn
        435                 440                 445
Pro Ser Leu Gly Asn Gly Asp
    450                 455

<210> SEQ ID NO 7
<211> LENGTH: 1098
<212> TYPE: DNA
<213> ORGANISM: Triticum aestivum

<400> SEQUENCE: 7
gcacgagatt cctcagggct tccgcttcgc cgtcgacttg cctgacggcc cttcgcgtgg      60
ctatgtttcc gagatcttcg gcgcccattt ccagctccct gatcttggtc cgatcggtgc     120
caacggtttg gcttcggcga gggatttcct ctcccccacg gcatggtacg agcaagccca     180
ccgccctggg tatgtcatag tgcagaagta tggtggtgag ctattcaccg ccacacagga     240
tttttcaccg tttaatgtgg tcgcctggca tggaaattat gtcccataca agtacgacct     300
gagcaagttc tgtccattta acactgtcct gttcgatcac gccgacccgt cagtaaacac     360
agttcttact gctccaactg acaagcctgg cgtagcatta cttgattttg tgatattccc     420
gccccgatgg ctggttgccg agaacacatt ccgccctccg tactaccatc gcaactgcat     480
gagcgagttc atgggactga ctacggcgt atacgaggca aaagccgatg gcttcctccc     540
cggaggcgcg agcctgcaca gctgcatgac accccatggg ccggacacca agacgtacga     600
```

```
ggcgaccatc agcaagcttg gcggaccgga ggccaacacg ccgacaaggc tgagcggcac      660
gctggccttc atgttcgagt ctgcgctgat cccacgcgtg tgccgctggg cgctcgagtc      720
accgtcccgg gacctcgact actaccagtg ttggatcggg ctcaaatccc acttctccca      780
cggcaaagat ggcagtgacg gacctgcgac aaccagcagc gacgacaagg atggcgagaa      840
gtagctctgt tcccgcaggt aggaaatgaa attcccaggc catgtatatg tatgtatact      900
actagttacc tgtgtaaagg gagaaagcaa acattaatca atccagtagg aataaataag      960
cagaatgtgc agcatgcatg tacaatcacc atccaacatg ccaatgtgta tagataataa     1020
tatcattagc aagcaaaagc atgtacattg atggtgatga gcagttggtt ttctttgctg     1080
gttagcagcc taaaaaaa                                                   1098
```

<210> SEQ ID NO 8
<211> LENGTH: 280
<212> TYPE: PRT
<213> ORGANISM: Triticum aestivum

<400> SEQUENCE: 8

```
His Glu Ile Pro Gln Gly Phe Arg Phe Ala Val Asp Leu Pro Asp Gly
  1               5                  10                  15

Pro Ser Arg Gly Tyr Val Ser Glu Ile Phe Gly Ala His Phe Gln Leu
                 20                  25                  30

Pro Asp Leu Gly Pro Ile Gly Ala Asn Gly Leu Ala Ser Ala Arg Asp
             35                  40                  45

Phe Leu Ser Pro Thr Ala Trp Tyr Glu Gln Ala His Arg Pro Gly Tyr
         50                  55                  60

Val Ile Val Gln Lys Tyr Gly Gly Glu Leu Phe Thr Ala Thr Gln Asp
 65                  70                  75                  80

Phe Ser Pro Phe Asn Val Val Ala Trp His Gly Asn Tyr Val Pro Tyr
                 85                  90                  95

Lys Tyr Asp Leu Ser Lys Phe Cys Pro Phe Asn Thr Val Leu Phe Asp
                100                 105                 110

His Ala Asp Pro Ser Val Asn Thr Val Leu Thr Ala Pro Thr Asp Lys
            115                 120                 125

Pro Gly Val Ala Leu Leu Asp Phe Val Ile Phe Pro Pro Arg Trp Leu
        130                 135                 140

Val Ala Glu Asn Thr Phe Arg Pro Pro Tyr Tyr His Arg Asn Cys Met
145                 150                 155                 160

Ser Glu Phe Met Gly Leu Ile Tyr Gly Val Tyr Glu Ala Lys Ala Asp
                165                 170                 175

Gly Phe Leu Pro Gly Gly Ala Ser Leu His Ser Cys Met Thr Pro His
            180                 185                 190

Gly Pro Asp Thr Lys Thr Tyr Glu Ala Thr Ile Ser Lys Leu Gly Gly
        195                 200                 205

Pro Glu Ala Asn Thr Pro Thr Arg Leu Ser Gly Thr Leu Ala Phe Met
    210                 215                 220

Phe Glu Ser Ala Leu Ile Pro Arg Val Cys Arg Trp Ala Leu Glu Ser
225                 230                 235                 240

Pro Ser Arg Asp Leu Asp Tyr Tyr Gln Cys Trp Ile Gly Leu Lys Ser
                245                 250                 255

His Phe Ser His Gly Lys Asp Gly Ser Asp Gly Pro Ala Thr Thr Ser
            260                 265                 270

Ser Asp Asp Lys Asp Gly Glu Lys
        275                 280
```

```
<210> SEQ ID NO 9
<211> LENGTH: 946
<212> TYPE: DNA
<213> ORGANISM: Zea mays

<400> SEQUENCE: 9
actccagtta atccaaattg gttttatctt ccaataggat acaatggacg agcatcatct      60
atagttgtgt ctggaaccga tgtaattagg cccagaggac aaggacatcc aacaggaaac     120
tccgctcctt attttggtcc ctctcagaag cttgattttg agcttgagat ggctgccatt     180
gttggtccag gaaatgaatt aggcaaacca attgatatca atgatgctga agaacatatt     240
tttgggccta actttgatga atgattggga gcgccagaga tattcaggct tgggagacta     300
tacctcttgg acctttcctt gggaaaagct tcagtaccac catatcacca tggattgtta     360
ctcttgatgc tttgaagcct tcatgtgtg aggctcctaa gcaggaaccc gaacctttac     420
catacctagc tgaaaagaat cacataaact atgacattcc tcttgaagtc ttgattaagc     480
ctaaagatca aatgttgca ctaattgtca caaaaactaa tttcaagcat ctgtattgga     540
cggtgacgca gcagctaaca caccacacta tcaatggatg caacatgagg ccgggggata     600
tatttgcaac tggcacactc agtggacctg aaccggactc cctcggatgt ctattgggag     660
ctaacatgga acgggcagaa ggagatacca gtgggcaatt tgacccgcaa gtttctagaa     720
gatggagatg agtcatcctg acaggatgct gcaagggtga agctacaaca ttggttttgg     780
aactgcactg ggaaggtcct gccggcactt ccctgagcca cacgtctttt acatcagttc     840
tcgagtccaa acactcaaca atctagcaag atgctatgta actgaacaac ggggggttgt     900
tttcgcatag gaaactgata ctctgttgtg aataaaaatc ggttca                    946

<210> SEQ ID NO 10
<211> LENGTH: 270
<212> TYPE: PRT
<213> ORGANISM: Zea mays

<400> SEQUENCE: 10

Thr Pro Val Asn Pro Asn Trp Phe Tyr Leu Pro Ile Gly Tyr Asn Gly
  1               5                  10                  15

Arg Ala Ser Ser Ile Val Val Ser Gly Thr Asp Val Ile Arg Pro Arg
             20                  25                  30

Gly Gln Gly His Pro Thr Gly Asn Ser Ala Pro Tyr Phe Gly Pro Ser
         35                  40                  45

Gln Lys Leu Asp Phe Glu Leu Glu Met Ala Ala Ile Val Gly Pro Gly
     50                  55                  60

Asn Glu Leu Gly Lys Pro Ile Asp Ile Asn Asp Ala Glu Glu His Ile
 65                  70                  75                  80

Leu Gly Leu Thr Leu Met Asn Asp Trp Ser Ala Arg Asp Ile Gln Ala
                 85                  90                  95

Trp Glu Thr Ile Pro Leu Gly Phe Leu Gly Lys Ser Phe Ser Thr
            100                 105                 110

Thr Ile Ser Pro Trp Ile Val Thr Leu Asp Ala Leu Lys Pro Phe Met
        115                 120                 125

Cys Glu Ala Pro Lys Gln Glu Pro Glu Pro Leu Pro Tyr Leu Ala Glu
    130                 135                 140

Lys Asn His Ile Asn Tyr Asp Ile Pro Leu Glu Val Leu Ile Lys Pro
145                 150                 155                 160
```

```
Lys Asp Gln Asn Val Ala Leu Ile Val Thr Lys Thr Asn Phe Lys His
                165                 170                 175
Leu Tyr Trp Thr Val Thr Gln Gln Leu Thr His His Thr Ile Asn Gly
            180                 185                 190
Cys Asn Met Arg Pro Gly Asp Ile Phe Ala Thr Gly Thr Leu Ser Gly
        195                 200                 205
Pro Glu Pro Asp Ser Leu Gly Cys Leu Leu Glu Leu Thr Trp Asn Gly
    210                 215                 220
Gln Lys Glu Ile Pro Val Gly Asn Leu Thr Arg Lys Phe Leu Glu Asp
225                 230                 235                 240
Gly Asp Glu Ser Ile Leu Thr Gly Cys Cys Lys Val Lys Leu Gln His
                245                 250                 255
Trp Phe Trp Asn Cys Thr Gly Lys Val Leu Pro Ala Leu Pro
                260                 265                 270

<210> SEQ ID NO 11
<211> LENGTH: 1533
<212> TYPE: DNA
<213> ORGANISM: Oryza sativa

<400> SEQUENCE: 11
gcacgagctt acatgtaagc tcgtgccgaa ttcggcacga gcttacacca ctgttcatct      60
gcgccacgac acgacacgac acgacacgag acgagagagg agtcggcaat ggcggagggg     120
tcgcggtcgc cgctgaggtc gttcgtggag gtggcgccgg ggtcgcactt ccccatccag     180
aacctcccct tcgggtctt ccgccgcagg ggctcgccgg agccggagcc gccgcgcccg     240
gccgtcgcca tcgggacttt cgcgctcgac ctcgccgccg tctccgacgc gggcctcttc     300
cacgggcccc tcctctccgc ctcccctgc ttccgccagg aaacgctcaa catgttcctg     360
gggatggggc gtccggcctg gaaggaggcg cgcgccacgc tgcagaagat cctctcagct     420
gatgagccgg ttttgcgtga caacgaggcc ttgaagaaga agtgccttgt tcccatgagc     480
gacacagaga tgcttctgcc aatcacggta ggagactaca ccgacttctt ttgttctgtg     540
caccatgcaa ggaattgtgg gttcatcttc cgtgggccac agaccccagt caacccaaat     600
tggtttcagc ttccagtagg ttatcatggt cgtgcatcct ctgtgattgt atctggaaca     660
gacatcattc gacccaaagg gcaaggccat ccaacaggag attctcgacc ttattttggt     720
ccttctaaga agcttgattt tgaacttgag atggcagcca ttgttggacc agggaatgaa     780
ttgggaaaac ctatcgatat taatgatgct gaagaacata tctttggcct aatgataatg     840
aatgattgga gtgccagaga tatccaagct tgggaaacta tacctcttgg accttttcctt     900
gggaaaagtt tcagtaccac agtatcaccc tggatcgtta ctatggatgc cctaaagcct     960
ttcacctgtg aagctcctaa gcaggaacct gaacctttgc cttacttagc tgaaaagaac    1020
cacgtaaact acgatattcc tcttgaggtc tggattaagc ccaaggagca agtgaacca    1080
tcaatggttg caaagagtaa cttcaagcat ctgtattgga ctttaacaca gcaactagca    1140
caccacactg ttaatggatg caatctgaga ccaggggata tgtttgcaac tggcacacta    1200
agcggacctg agacagaatc tttgggatgt tgctggagc taacatggaa tgggcagaag    1260
gagatatcag ttgaaactc gacccgcaag ttcctagaag atgggggatga ggtcatcttg    1320
acagcttgtt gcaagggtga aggctacaat gtcggattcg aacctgcac tgggaaggtt    1380
ctgcctgcac ttccatgatc caacatatag aggataacct gctttcatct catcagtgtg    1440
tcaataatct ctgaaaaaag catgcaatga ggcaatgtat ccagctagtt acatcaatat    1500
```

-continued tttaatgcct agtgatggga aaaatactaa taa 1533

<210> SEQ ID NO 12
<211> LENGTH: 429
<212> TYPE: PRT
<213> ORGANISM: Oryza sativa

<400> SEQUENCE: 12

```
Met Ala Glu Gly Ser Arg Ser Pro Leu Arg Ser Phe Val Glu Val Ala
 1               5                  10                  15

Pro Gly Ser His Phe Pro Ile Gln Asn Leu Pro Phe Gly Val Phe Arg
            20                  25                  30

Arg Arg Gly Ser Pro Glu Pro Glu Pro Pro Arg Pro Ala Val Ala Ile
        35                  40                  45

Gly Asp Phe Ala Leu Asp Leu Ala Ala Val Ser Asp Ala Gly Leu Phe
    50                  55                  60

His Gly Pro Leu Leu Ser Ala Ser Pro Cys Phe Arg Gln Glu Thr Leu
65                  70                  75                  80

Asn Met Phe Leu Gly Met Gly Arg Pro Ala Trp Lys Glu Ala Arg Ala
                85                  90                  95

Thr Leu Gln Lys Ile Leu Ser Ala Asp Glu Pro Val Leu Arg Asp Asn
            100                 105                 110

Glu Ala Leu Lys Lys Lys Cys Leu Val Pro Met Ser Asp Thr Glu Met
        115                 120                 125

Leu Leu Pro Ile Thr Val Gly Asp Tyr Thr Asp Phe Phe Cys Ser Val
    130                 135                 140

His His Ala Arg Asn Cys Gly Phe Ile Phe Arg Gly Pro Gln Thr Pro
145                 150                 155                 160

Val Asn Pro Asn Trp Phe Gln Leu Pro Val Gly Tyr His Gly Arg Ala
                165                 170                 175

Ser Ser Val Ile Val Ser Gly Thr Asp Ile Ile Arg Pro Lys Gly Gln
            180                 185                 190

Gly His Pro Thr Gly Asp Ser Arg Pro Tyr Phe Gly Pro Ser Lys Lys
        195                 200                 205

Leu Asp Phe Glu Leu Glu Met Ala Ala Ile Val Gly Pro Gly Asn Glu
    210                 215                 220

Leu Gly Lys Pro Ile Asp Ile Asn Asp Ala Glu His Ile Phe Gly
225                 230                 235                 240

Leu Met Ile Met Asn Asp Trp Ser Ala Arg Asp Ile Gln Ala Trp Glu
                245                 250                 255

Thr Ile Pro Leu Gly Pro Phe Leu Gly Lys Ser Phe Ser Thr Thr Val
            260                 265                 270

Ser Pro Trp Ile Val Thr Met Asp Ala Leu Lys Pro Phe Thr Cys Glu
        275                 280                 285

Ala Pro Lys Gln Glu Pro Glu Pro Leu Pro Tyr Leu Ala Glu Lys Asn
    290                 295                 300

His Val Asn Tyr Asp Ile Pro Leu Glu Val Trp Ile Lys Pro Lys Glu
305                 310                 315                 320

Gln Ser Glu Pro Ser Met Val Ala Lys Ser Asn Phe Lys His Leu Tyr
                325                 330                 335

Trp Thr Leu Thr Gln Gln Leu Ala His His Thr Val Asn Gly Cys Asn
            340                 345                 350

Leu Arg Pro Gly Asp Met Phe Ala Thr Gly Thr Leu Ser Gly Pro Glu
        355                 360                 365
```

```
Thr Glu Ser Leu Gly Cys Leu Leu Glu Leu Thr Trp Asn Gly Gln Lys
    370                 375                 380

Glu Ile Ser Val Gly Asn Ser Thr Arg Lys Phe Leu Glu Asp Gly Asp
385                 390                 395                 400

Glu Val Ile Leu Thr Ala Cys Cys Lys Gly Glu Gly Tyr Asn Val Gly
                405                 410                 415

Phe Gly Thr Cys Thr Gly Lys Val Leu Pro Ala Leu Pro
            420                 425

<210> SEQ ID NO 13
<211> LENGTH: 1528
<212> TYPE: DNA
<213> ORGANISM: Glycine max

<400> SEQUENCE: 13
gcacgagtct cggtccagtg tctctttcaa agtgctgctg ctgccagcat tgacctgagc      60
tagagcagta accgtcatca ccactgccag tacggtacca tggctgtgct tcaatctttc    120
gtttcggtcc acccagattc tcacttcccc atacagaacc tcccctacgg agtgttcaag    180
ccccaatccg cttctcctcc tcgtcccggc gtcgccatcg agacttcgt cctcgacctc      240
tccgaaatct cttccgctgg tctcttcgac ggccctctcc tcaaaaactc cgattgcttc    300
ctccagccta atctaaataa gtttgtatca ctgggaaggc cagcttggaa ggaagctcgt    360
gccactcttc aaaagctttt atcagcaact gagccaacct tgaggacaa cgtggttttg      420
aggcagaaat cactactgcc tgtgagtact gtggagttgc ttctccctgt tgttgttggg    480
gactataccg atttctttac gtctctgcat cacactaaaa attgtgggct cattttcgt      540
gggccacaga ctcctgttct agataattgg tatcgcctgc ctgttgccta ccatggacga    600
gcatcttctg ttgttatttc cggaacagat attgttcggc aagaggtca agctcatcca      660
attggcagct ctactcccta ctttggccct tcattaaagc tagactttga gttggaaatg    720
gctactattg ttggacctgg aaatgaattg ggaaaacctg ttgatattaa caatgctgaa    780
gatcacatct ttgacttgt tgtaatgaac gattggagtg ctcgagatat tcaggcatgg      840
gaatatattc ctcttggtcc ttttcttggc aagagttttg gaacaacaat atcaccttgg    900
attgtgacct tggaagcatt agaaccttt gcttgcgaag ccccaaaaca ggatcctcct      960
ccacttccat acttgactga aaaagtatcc agaatctatg atatttccct agaggctcac   1020
ataaaacctg cggggcatga agattcaggt gtggtgtcac ggactaatct aaagcactta   1080
tattggacat tgacccaaca acttgctcac catacaatca acgttgcaa ccttaggcca    1140
ggcgatctcc tcggaactgg gacagttagt ggtcctgagc cggagtcccg ggcatgcttg   1200
ctagaattaa cgtggaatgg acaaaacgcg gtaccagtga atgggttaaa taagaaattt   1260
cttgaagatg gggatgaagt tatcttaact ggatattgca agggaaatgg ctacactatt   1320
gggtttggta cctgctcggg caagattgtt cccgcagctc cctgaggtca gtatcatttc   1380
atagtcttta ccagttgtgg tgggaggagt tgtagaatca agtatctggc tcctttccac   1440
atagcgtgtt ttatttactc ggctcataat ttgactttaa taaagctggt gttttatatt   1500
tttcttttta aaaaaaaaa aaaaaaaa                                        1528

<210> SEQ ID NO 14
<211> LENGTH: 421
<212> TYPE: PRT
<213> ORGANISM: Glycine max

<400> SEQUENCE: 14
```

```
Met Ala Val Leu Gln Ser Phe Val Ser Val His Pro Asp Ser His Phe
 1               5                  10                  15

Pro Ile Gln Asn Leu Pro Tyr Gly Val Phe Lys Pro Gln Ser Ala Ser
                20                  25                  30

Pro Pro Arg Pro Gly Val Ala Ile Gly Asp Phe Val Leu Asp Leu Ser
             35                  40                  45

Glu Ile Ser Ser Ala Gly Leu Phe Asp Gly Pro Leu Leu Lys Asn Ser
         50                  55                  60

Asp Cys Phe Leu Gln Pro Asn Leu Asn Lys Phe Val Ser Leu Gly Arg
 65                  70                  75                  80

Pro Ala Trp Lys Glu Ala Arg Ala Thr Leu Gln Lys Leu Leu Ser Ala
                 85                  90                  95

Thr Glu Pro Thr Leu Arg Asp Asn Val Val Leu Arg Gln Lys Ser Leu
            100                 105                 110

Leu Pro Val Ser Thr Val Glu Leu Leu Pro Val Val Gly Asp
            115                 120                 125

Tyr Thr Asp Phe Phe Thr Ser Leu His His Thr Lys Asn Cys Gly Leu
        130                 135                 140

Ile Phe Arg Gly Pro Gln Thr Pro Val Leu Asp Asn Trp Tyr Arg Leu
145                 150                 155                 160

Pro Val Ala Tyr His Gly Arg Ala Ser Ser Val Val Ile Ser Gly Thr
                165                 170                 175

Asp Ile Val Arg Pro Arg Gly Gln Ala His Pro Ile Gly Ser Ser Thr
            180                 185                 190

Pro Tyr Phe Gly Pro Ser Leu Lys Leu Asp Phe Glu Leu Glu Met Ala
        195                 200                 205

Thr Ile Val Gly Pro Gly Asn Glu Leu Gly Lys Pro Val Asp Ile Asn
210                 215                 220

Asn Ala Glu Asp His Ile Phe Gly Leu Val Val Met Asn Asp Trp Ser
225                 230                 235                 240

Ala Arg Asp Ile Gln Ala Trp Glu Tyr Ile Pro Leu Gly Pro Phe Leu
            245                 250                 255

Gly Lys Ser Phe Gly Thr Thr Ile Ser Pro Trp Ile Val Thr Leu Glu
        260                 265                 270

Ala Leu Glu Pro Phe Ala Cys Glu Ala Pro Lys Gln Asp Pro Pro Pro
        275                 280                 285

Leu Pro Tyr Leu Thr Glu Lys Val Ser Arg Ile Tyr Asp Ile Ser Leu
        290                 295                 300

Glu Ala His Ile Lys Pro Ala Gly His Glu Asp Ser Gly Val Val Ser
305                 310                 315                 320

Arg Thr Asn Leu Lys His Leu Tyr Trp Thr Leu Thr Gln Gln Leu Ala
            325                 330                 335

His His Thr Ile Asn Gly Cys Asn Leu Arg Pro Gly Asp Leu Leu Gly
            340                 345                 350

Thr Gly Thr Val Ser Gly Pro Glu Ser Arg Ala Cys Leu Leu
        355                 360                 365

Glu Leu Thr Trp Asn Gly Gln Asn Ala Val Pro Val Asn Gly Leu Asn
        370                 375                 380

Lys Lys Phe Leu Glu Asp Gly Asp Glu Val Ile Leu Thr Gly Tyr Cys
385                 390                 395                 400
```

-continued

```
Lys Gly Asn Gly Tyr Thr Ile Gly Phe Gly Thr Cys Ser Gly Lys Ile
            405                 410                 415

Val Pro Ala Ala Pro
            420
```